(12) United States Patent
Canfield et al.

(10) Patent No.: US 7,239,921 B2
(45) Date of Patent: Jul. 3, 2007

(54) HOUSING FOR AN IMPLANTABLE MEDICAL DEVICE

(75) Inventors: David L. Canfield, Lake Hughes, CA (US); Kate E. Purnell, Valencia, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 593 days.

(21) Appl. No.: 10/601,723

(22) Filed: Jun. 23, 2003

(65) Prior Publication Data

US 2004/0260372 A1 Dec. 23, 2004

(51) Int. Cl.
*A61N 1/00* (2006.01)

(52) U.S. Cl. ....................................................... 607/48

(58) Field of Classification Search .................. 607/36, 607/48, 60
See application file for complete search history.

(56) References Cited

U.S. PATENT DOCUMENTS

| | | | | |
|---|---|---|---|---|
| 4,041,955 A | * | 8/1977 | Kelly et al. | .................... 607/36 |
| 4,071,032 A | * | 1/1978 | Schulman | .................... 607/36 |
| 4,333,469 A | * | 6/1982 | Jeffcoat et al. | ................. 607/5 |
| 4,712,555 A | | 12/1987 | Thornander et al. | |
| 5,324,316 A | | 6/1994 | Schulman et al. | |
| 5,405,367 A | | 4/1995 | Schulman et al. | |
| 6,026,818 A | | 2/2000 | Blair et al. | |
| 6,081,070 A | | 6/2000 | Popov et al. | |
| 6,164,284 A | * | 12/2000 | Schulman et al. | .......... 128/899 |
| 6,208,894 B1 | | 3/2001 | Schulman et al. | |
| 6,245,092 B1 | * | 6/2001 | Schaldach, Jr. | ................ 607/1 |
| 6,315,721 B2 | | 11/2001 | Schulman et al. | |
| 7,177,698 B2 | * | 2/2007 | Klosterman et al. | .......... 607/60 |
| 2002/0042637 A1 | | 4/2002 | Stover | |

FOREIGN PATENT DOCUMENTS

EP 1048324 10/2002

\* cited by examiner

*Primary Examiner*—George Manuel
(74) *Attorney, Agent, or Firm*—Malcolm J. Romano

(57) ABSTRACT

A housing for an implantable medical device in the shape of a hollow magnetic field concentrating tube about which an electrically conductive wire coil is wound and within which medical device electronics is housed. The tube, preferably made of ferrite, is encased in a protective sleeve formed of a material that is impervious to body fluids. The coil provides an electrical output as a result of being exposed to a varying magnetic field that is concentrated around the coil by virtue of the field concentrating tube. The output of the coil is utilized as part of a power supply for the medical device electronics. The sleeve has a generally cylindrical cross-section having an outside diameter of about 3.175 mm and an axial length in the range of about 3.2 mm to 8 mm.

25 Claims, 4 Drawing Sheets

HOUSING FOR AN IMPLANTABLE MEDICAL DEVICE

FIELD OF THE INVENTION

The present invention relates to a housing for the electronics of an implantable medical device, more specifically, a housing formed of a material capable of concentrating a magnetic field to which the housing is exposed.

BACKGROUND

Implantable medical devices for remedial treatment of and compensation for cardiac, neural and muscular deficiencies are known in the art. These devices range from cardiac pacemakers as described in U.S. Pat. No. 4,712,555 to Thornander et al., to microstimulators as described in U.S. Pat. No. 6,208,894 to Schulman et al. The quest for minimization of such devices has provided, at least in the area of microstimulators, cylindrically shaped devices that range in size of about 6 mm in diameter and about 60 mm in axial length, see for example the device described in U.S. Pat. No. 6,315,721 ('721). The device described in '721 is configured so that, the electronics is packaged in a housing in tandem with a wire wound ferrite core used as a source of recharging energy for the device electronics power supply. Furthermore, the electronics themselves is arranged in a lengthwise fashion within the device, thereby adding to the overall length of the device. This configuration ultimately gives rise to the stated overall device length. In view of the implant nature of such medical devices, even still further device miniaturization would prove advantageous to device implantation and extraction (if required), as well as patient comfort.

SUMMARY OF THE INVENTION

The present invention addresses the quest for further miniaturization and provides a novel packaging and configuration of the medical device electronics within a wire wound hollow tube that markedly reduces the overall dimension of the device. In accordance with the invention, a hollow tube formed of a magnetic field concentrating material, such as ferrite, houses the device electronics. An electrically conductive wire coil is wound around the hollow tube and serves to generate time varying electrical signals when exposed to a time varying magnetic field. Since the hollow tube material concentrates the magnetic field to which the medical device is exposed, the resultant electrical signal generated by the coil, when exposed to the magnetic field, is maximized. In particular, because of what is known as the "skin effect", a majority of the magnetic field concentrating effect of a ferrite tube is in the outermost region of the tube. The wire coil is positioned to be in proximity to the concentrated magnetic field. By virtue of the coil and hollow tube arrangement, the interior region of the hollow tube is essentially free of magnetic field effects and therefore an excellent candidate for containing the medical device electronics. Moreover, the volume of the ferrite to produce the described magnetic field is minimized.

In accordance with an aspect of the invention, the medical device electronics, in the form of a plurality of Integrated Circuit (IC) chips, are mounted to a flexible (flex) circuit having a network of interconnecting electrical vias or conductors positioned to accommodate interconnection between respective ones of the terminals of the IC chips. Due to the flexible nature of the flex circuit, the circuit is foldable to achieve a "U" shaped profile with the IC chips in face-to-face arrangement. Accordingly, the equivalent length of the IC chip loaded flex circuit is essentially reduced to about one-half of predecessor designs. The IC chip thickness is such that, with the flex circuit in the folded configuration, the flex circuit fits neatly into the interior region of the hollow tube.

A protective sleeve encases the hollow tube and has fluid tight hermetically sealed end caps to insulate the device from body fluids. The sleeve is formed of a material, such as a ceramic, that is impervious to body fluids. Electrically conductive electrodes are mounted on the sleeve end caps for delivery of stimulation energy, generated by the device electronics, to body tissue with which they are in contact. The electrodes may also serve as antennae's for wireless communication with an external programming device.

A potting matrix formed preferably of silicone, including a getter, is injected into the interior region of the hollow tube to fill any voids existing between the device electronics and the interior of the hollow tube. The matrix prevents the electronics from moving relative to the hollow tube and also provides a hermetically sealed environment for the device electronics.

BRIEF DESCRIPTION OF THE DRAWINGS

The above and other aspects, features and advantages of the present invention will become apparent from the following more particular description thereof presented in conjunction with the following drawings, wherein.

DESCRIPTION OF THE PREFERRED EMBODIMENTS

The present invention is directed to a housing for an implantable medical device or microstimulator intended for implant beneath a patient's skin for the purpose of stimulation, parameter monitoring and data exchange. The stimulation function may, for example, be neural or muscular and the data exchange may be by way of a radio frequency (RF) communication link between the medical device and an external RF transmitter/receiver device. This description should not be taken in a limiting sense but rather for the purpose of describing the general principles of the invention.

Figure 1:
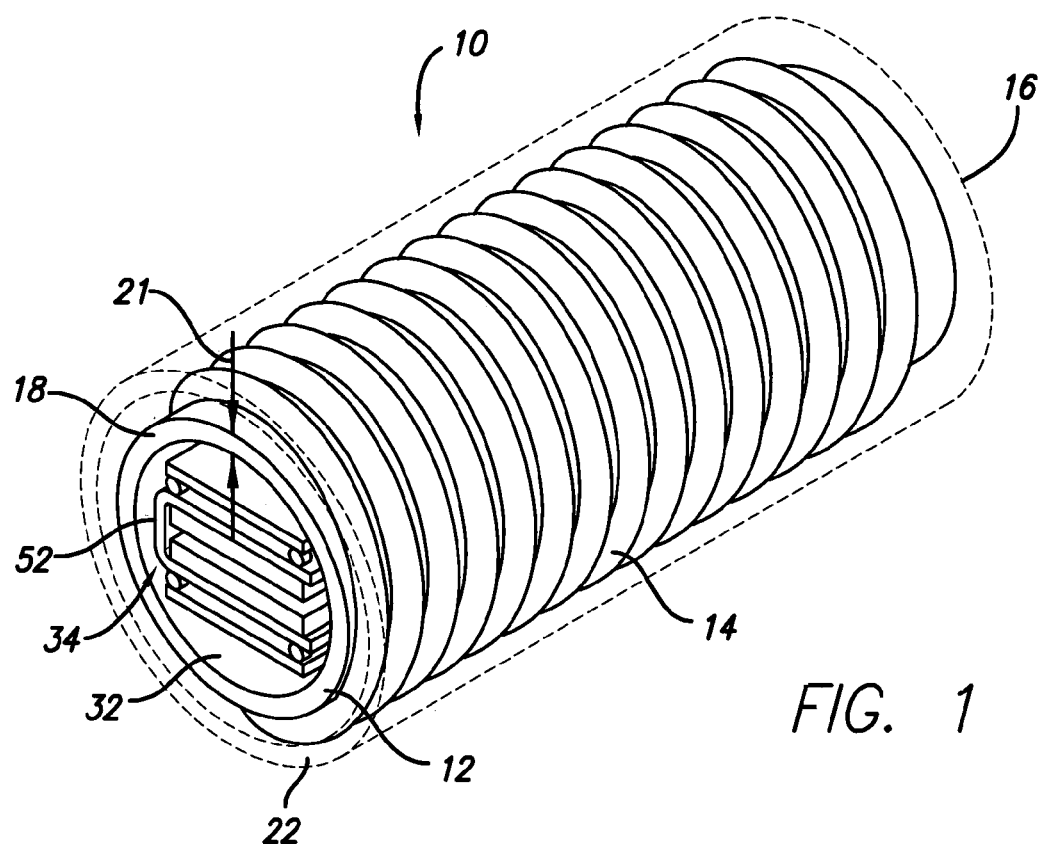
FIG. 1 is a perspective view, in partial phantom, of an embodiment of the present invention.
Figure 2:
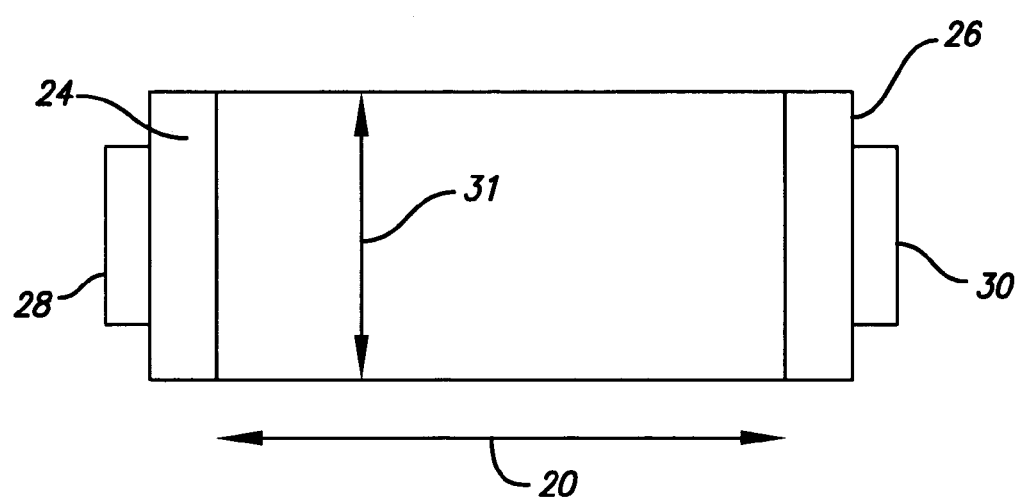
FIG. 2 is a side view of the embodiment of FIG. 1 including end caps.

Referring now to FIG. 1, there is shown a perspective view of an embodiment of the medical device housing 10 of the present invention. The housing 10 includes an elongated hollow, essentially cylindrically shaped tube 12. Although the description is in terms of a cylindrical shape, it is to be understood that alternate shapes such as, for example, oval or square, are appropriate substitutes for the housing shape. The tube 12 is formed of a magnetic field condensing or concentrating material such as iron or a ferrous derivative. The preferred material is ferrite, due to its greater ability to concentrate magnetic fields to which it is exposed, in an area in and around the object formed of the ferrite. More specifically, the hollow ferrite tube provides a dense magnetic field localized at the outermost region of the tube due to the realized magnetic "skin effect". Wrapped around hollow tube 12 is coil 14 formed of a thin electrically conductive filament wire typically being about forty-four (44) gauge. The coil 14 extends the length of the hollow tube 12 between tube ends 16 and 18 and has turns numbering in the range of about 10 to 600. In one configuration, the coil may be wound in multiple layers such that the over winding nestles in the region between and in contact with two adjacent under windings, so that the dimension across the over and under windings is somewhat less than twice the diameter of filament wires. The hollow tube has an axial length 20 (as shown in FIG. 2 encased in sleeve 22) of about 3 mm with the tube having an outside diameter of about 2.26 mm and an inside diameter of about 1.78 mm. The hollow tube wall thickness dimension 21, measured radially, is about 0.24 mm.

A protective sleeve 22 (shown in phantom in FIG. 1) encases the hollow tube 12 along its length with the sleeve having fluid tight hermetically sealed end caps 24 and 26. The sleeve 22 has a generally cylindrical cross-section and is formed of a material, such as ceramic, impervious to body fluids and accordingly the interior of the housing remains insulated from exposure to such body fluids. The end caps 24 and 26 may be electrically conductive to serve as stimulation electrodes, sensor electrodes and/or antennas as part of the RF communication link. The end caps 24 and 26 may be brazed onto the sleeve 22 and electrically conductive plates 28 and 30 provide an electrical connection with body tissue to which they are in contact and may be laser welded onto end caps 24 and 26 respectively, in a manner as taught in U.S. Pat. No. 6,185,452, incorporated herein by reference, in its entirety. Conductive plates 28 and 30 may be formed of platinum, iridium or platinum-iridium to minimize the contact impedance of the medical device electrodes with body tissue. Sleeve 22 has an outside diameter 31 of about 3.175 mm, which is about one-half the dimension of predecessor devices (see U.S. Pat. No. 6,315,721 incorporated herein by reference, in its entirety) and an axial length in the range of about 3.2 mm to 8 mm depending upon the desired amount of additional electrical circuitry, beyond that shown in FIG. 1, to be included in the housing. In this regard, the device of the present invention may be inserted beneath the skin of a patient by the use of a hypodermic type insertion tool (not shown) with greater ease and expediency than previously known.

Figure 3:
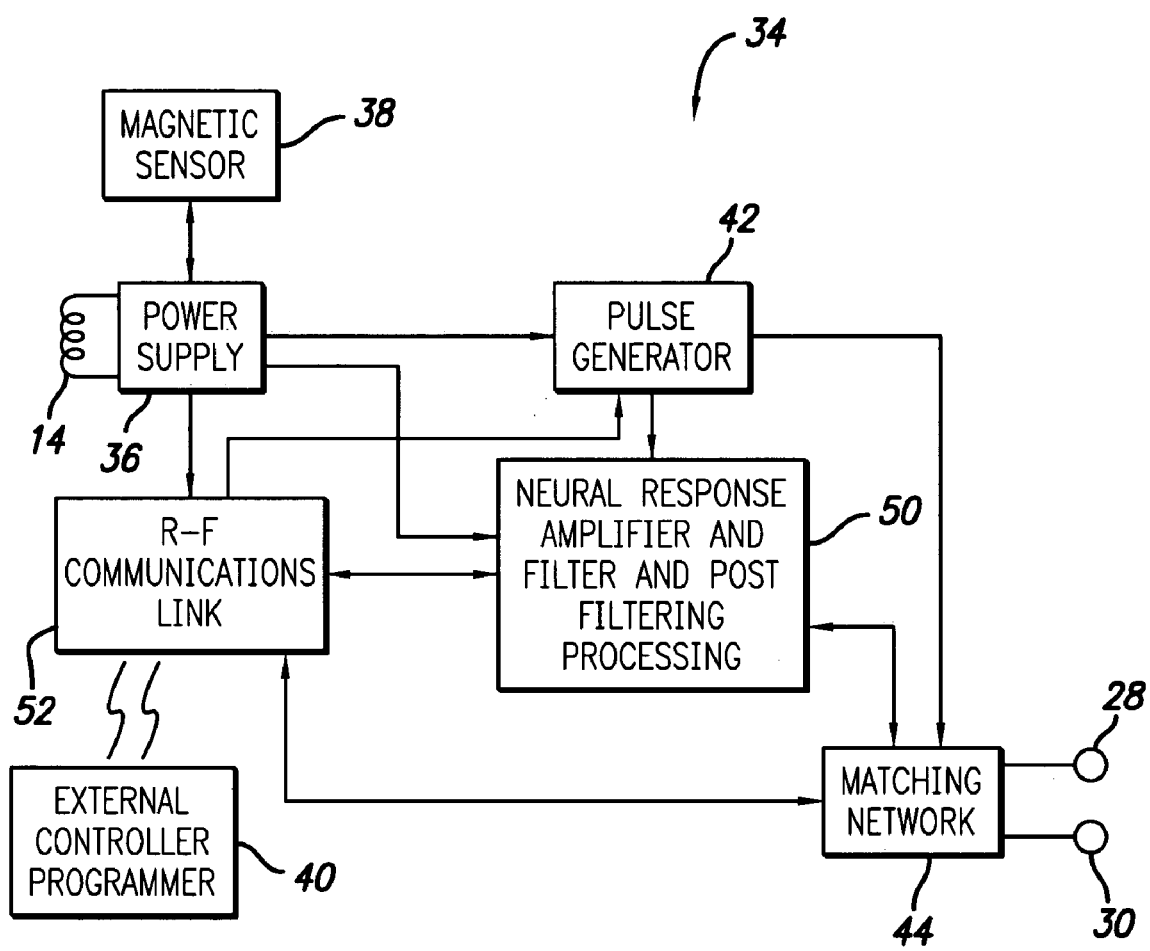
FIG. 3 is a block diagram of the electronic modules of the embodiment of FIG. 1.

Housed within the hollow tube interior region 32 are device electronics 34. The device electronics comprises those modules necessary to carry out the stimulation, sensing and communication functions necessary for successful operation of the medical device (microstimulator). More specifically, and with reference to FIG. 3, there is shown in block diagram format, the component parts of the device electronics. The coil 14 is coupled to power supply 36 that supplies power to the individual circuits of the device. The power supply 36 includes rectifier circuitry and storage capacitors (not shown) to convert the time varying signal provided by coil 14 to a direct current signal for use by the other circuits. A magnetic sensor 38 is coupled to power supply 36 and serves to disable the power supply upon exposure of the sensor 38 to a strong magnetic field provided by a magnet when it is positioned in proximity to the medical device. This feature allows the medical device to be disabled once it has been determined that the device and device electronics should be shut down. An R-F communication link module 52 serves to provide a communication link by means of wireless communication with an external controller 40. The external programmer 40 provides programming information to program the medical device when to provide specific stimulation pulses, sense biological parameters and monitor neural responses. The pulse generator 42, in response to instructions received from the communications link 52, provides pre-selected tissue stimulation pulses via matching network 44 and conductive plates 28 and 30. The conductive plates 28 and 30 are positioned to be in contact with the desired tissue to be stimulated. A neural response amplifier and filter 50 amplifies and filters neural response signals received from plates 28 and 30 for transmission to the external controller 40 via communication link 40.

Figure 5:
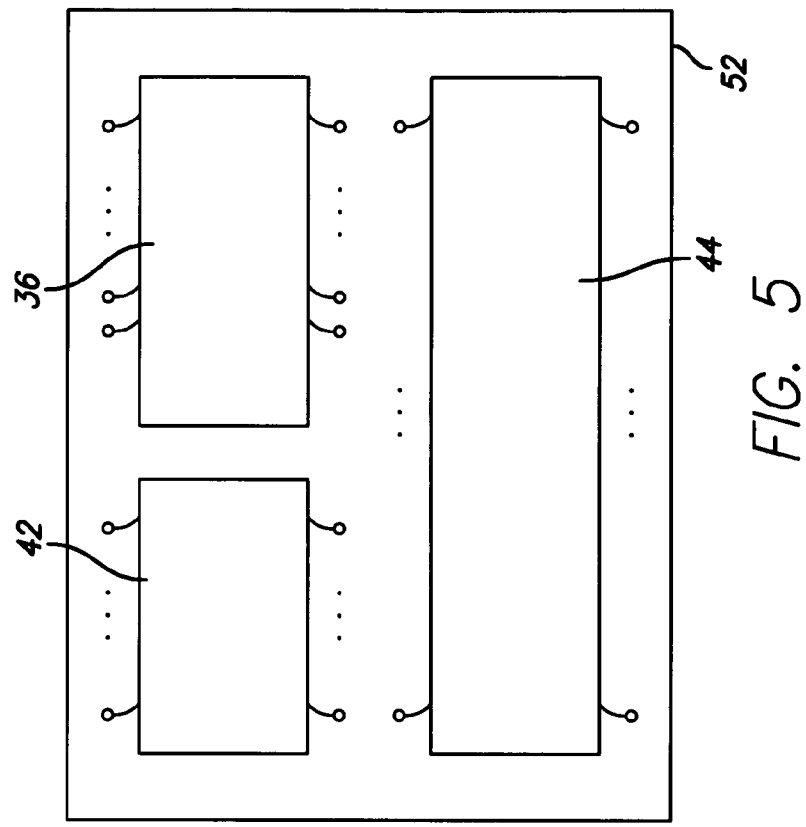
FIG. 5 is a simplified view of the other side of the flex circuit of the embodiment of FIG. 4, upon which device electronics IC chips are mounted.
Figure 4:
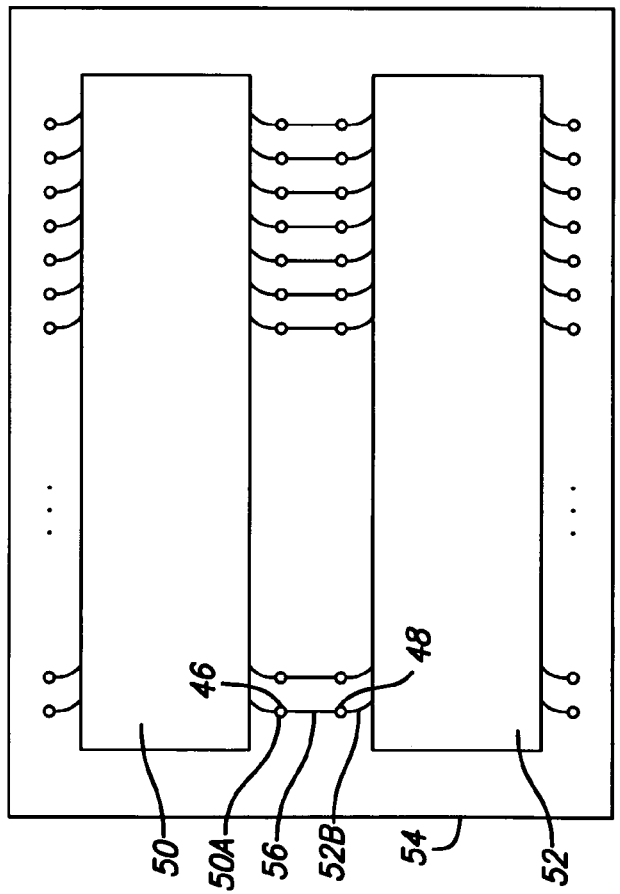
FIG. 4 is a simplified schematic view of one side of a flex circuit of the embodiment of FIG. 1, upon which device electronics IC chips are mounted.
Figure 6:
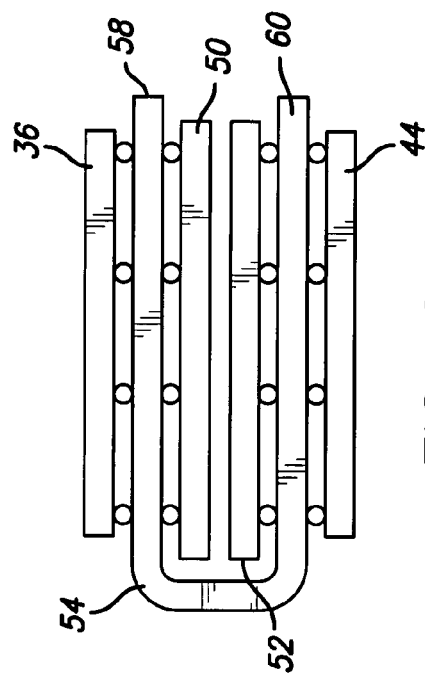
FIG. 6 is a partial side elevation view of the flex circuit of FIGS. 4 and 5, mounted with IC chips and in the folded configuration.
Figure 7:
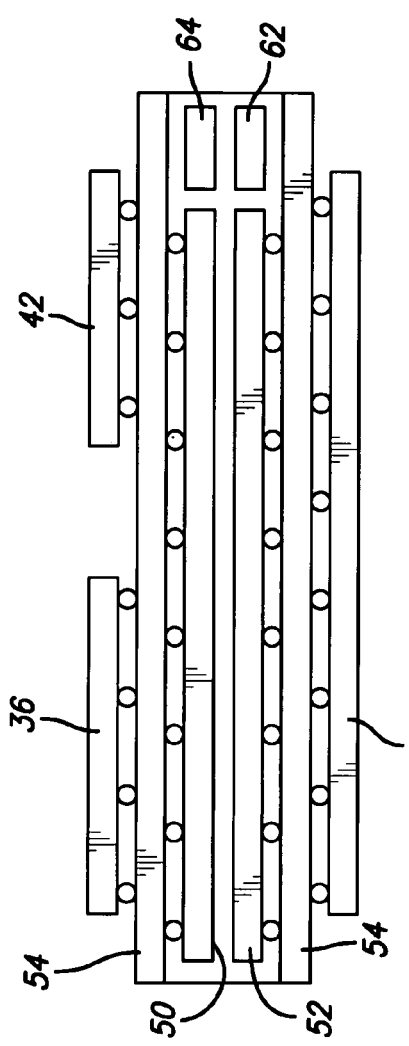
FIG. 7 is a partial front elevation view of the embodiment of FIG. 6.

The device electronics comprises a plurality of integrated circuit (IC) chips interconnected by means of a flexible interconnecting circuit (flex circuit) 54 that includes a plurality of electrical conductors arranged for electrically interconnecting the plurality of IC chips. More specifically and referring to FIG. 4, there is shown in schematic format, the flex circuit 54 in a flat open face up position upon which is mounted two IC chips 50 and 52. A representative interconnect between two IC chips is shown wherein a breakout 50A representing a signal line from IC chip 50 is connected to flex circuit terminal 46 and a breakout 52B representing a signal line from IC chip 52 is connected to flex circuit terminal 48 and an electrical flex circuit wire 56 electrically interconnects the breakouts so that they are in electrical communication with each other. Securing the breakouts to the corresponding flex circuit terminals may be accomplished by techniques known in the art, such as spot welding or soldering. The opposite face of the flex circuit 54 is shown in FIG. 5 with three IC chips 36, 42 and 44 mounted in a manner similar to that shown in FIG. 4. Any interconnects between IC chips on opposite faces of the flex circuit 54 may be accomplished by means of electrical conductors extending through the flex circuit. The flex circuit 54 is formed preferably of a flexible material such as a bendable plastic derivative to which may be adhered or imbedded, a plurality of electrical conductors in a manner known in the art. FIG. 6 illustrates the bendable nature of the flex circuit 54 where the flex circuit is bent along a central axis (not shown) so that the resultant circuit configuration is in a "U" shape with the ends 58 and 60 of the flex circuit, although not a requirement, being essentially in registration. FIG. 7 is a front elevation view of an alternate embodiment of the device of FIG. 6, showing the addition of electronic components such as capacitor 62 adapted for the delivery of a large amount of stimulation charge to tissue by means of conductive plates 28 and 30 and diode 64 used in the power supply module 36 for rectifying the time varying signal provided by coil 14. In all embodiments, the entire medical device electronic circuitry is housed within the interior region of the hollow tube 12. The advantage to this novel configuration is the resultant economy of size providing an overall reduction in geometry of the medical device.

Subsequent to positioning of the device electronics within the hollow tube 12, a potting matrix, preferably of silicon with a getter, is introduced into the interior region 32 to fill any voids existing between the device electronics and the inner wall of the hollow tube 12. The potting matrix tends to stabilize the device electronics within the interior region against relative movement between the electronics and hollow tube and the getter provides, among other things, increased hermeticity of the electronics.

What is claimed is:

1. A housing for a microstimulator adapted to be implanted in body tissue by expulsion through a hypodermic needle, the microstimulator housing comprising:
   a cylindrical tube formed as a unitary structure solely of ferrite, said ferrite tube having a length, said ferrite tube further having an interior region adapted to receive microstimulator circuit elements;
   an electrically conductive coil wound around an outer surface of said ferrite tube; and
   an outer, cylindrical protective sleeve encasing the ferrite tube and the coil, the sleeve being formed of a non-magnetic material impervious to body fluids and having opposed, sealed ends so as to isolate the ferrite tube from contact with said body fluids.

2. The housing of claim 1 wherein the sleeve is formed of a ceramic material.

3. The housing of claim 1 wherein the ferrite tube has an outer diameter of about 2.26 mm and an inner diameter of about 1.78 mm.

4. The housing of claim 1 wherein the ferrite tube has an axial length of about 3 mm.

5. The housing of claim 1 wherein the sleeve has an outer diameter ranging from about 3.2 mm to about 8.0 mm.

6. The housing of claim 1 wherein the coil comprises a winding having about 10 to about 600 turns.

7. The housing of claim 1 wherein the coil is formed of wire having a size of about 44 gauge.

8. A microstimulator adapted to be implanted in body tissue by expulsion through a hypodermic needle, the microstimulator comprising:
   an elongated cylindrical tube formed as a unitary structure solely of ferrite and having an interior region;
   an electrically conductive coil wound around an outer surface of said ferrite tube;
   microstimulator circuit elements disposed substantially completely within the confines of said interior region of said ferrite tube, said coil being adapted to electrically communicate with said microstimulator circuit elements; and
   an outer, cylindrical, protective sleeve encasing the ferrite tube and the coil, the sleeve having an outer configuration facilitating implantation of said microstimulator through said hypodermic needle, the sleeve being formed of a non-magnetic material impervious to body fluids and having opposed sealed ends so as to isolate the ferrite tube and the coil from contact with said body fluids.

9. The microstimulator of claim 8 wherein said ferrite tube has a length, and wherein said protective sleeve has a length substantially coextensive with the length of the ferrite tube.

10. The microstimulator of claim 8 wherein the microstimulator circuit elements comprise at least one integrated circuit (IC) chip in electrical communication with said coil.

11. The microstimulator of claim 10 wherein the microstimulator circuit elements comprise at least two IC chips, the at least two IC chips being electrically interconnected.

12. The microstimulator of claim 11 wherein the at least two IC chips are electrically interconnected by an electrically conductive flex circuit.

13. The microstimulator of claim 12 wherein a selected electrical terminal contact on one of said at least two IC chips is electrically connected to a selected electrical terminal contact on the other of said at least two IC chips by said flex circuit.

14. The microstimulator of claim 12 wherein said at least two IC chips are positioned in close proximity by said flex circuit.

15. The microstimulator of claim 14 wherein the flex circuit is folded to position said at least two IC chips in confronting relationship.

16. The microstimulator of claim 8 wherein the interior of the ferrite tube includes a silicone potting matrix substantially filling any voids within the tube surrounding said microstimulator circuit elements.

17. The microstimulator of claim 16 wherein the potting matrix includes a getter for absorbing any moisture introduced into said ferrite tube.

18. The microstimulator of claim 8 wherein the microstimulator circuit elements include electrical elements powered by a rechargeable battery, the electrical elements including a rectifier circuit coupled to the rechargeable battery, said rectifier circuit being in electrical communication with the coil, whereby exposure of the coil to a varying magnetic field causes electric currents to be generated within the coil and rectified in a manner to recharge the battery.

19. The microstimulator of claim 8 wherein the microstimulator circuit elements include radio frequency (RF) transmission and receiver circuitry and wherein the coil is electrically coupled to and adapted to communicate with the RF circuitry as an antenna therefor.

20. The microstimulator of claim 8 wherein the sleeve is formed of a ceramic material.

21. The microstimulator of claim 8 wherein the tube has an outer diameter of about 2.26 mm and an inner diameter of about 1.78 mm.

22. The microstimulator of claim 8 wherein the ferrite tube has an axial length of about 3 mm.

23. The microstimulator of claim 8 wherein the sleeve has an outer diameter ranging from about 3.2 mm to about 8.0 mm.

24. The microstimulator of claim 8 wherein the coil comprises from about 10 to about 600 turns.

25. The microstimulator of claim 8 wherein the coil is formed of wire having a size of about 44 gauge.

* * * * *